United States Patent [19]

DiVito

[11] Patent Number: 4,672,953
[45] Date of Patent: Jun. 16, 1987

[54] ORAL HYGIENE APPARATUS

[76] Inventor: Enrico E. DiVito, 15001 N. 46th Pl., Phoenix, Ariz. 85032

[21] Appl. No.: 741,860

[22] Filed: Jun. 6, 1985

[51] Int. Cl.$^4$ .............................................. A46B 11/06
[52] U.S. Cl. .................................. 128/66; 128/62 A; 433/80; 433/91; 433/100
[58] Field of Search .................. 128/62 A, 66; 433/80, 433/91, 95, 84, 85, 100; 604/22, 27, 32, 33, 34, 35, 48, 313; 15/167 R

[56] References Cited

U.S. PATENT DOCUMENTS

| | | | |
|---|---|---|---|
| 3,208,145 | 9/1965 | Turner | 433/95 |
| 4,175,879 | 11/1979 | Molinari | 128/66 |
| 4,425,115 | 1/1984 | Wuehinich | 604/22 |
| 4,538,631 | 9/1985 | Prince | 433/91 |

*Primary Examiner*—John J. Wilson
*Attorney, Agent, or Firm*—Herbert E. Haynes, Jr.

[57] ABSTRACT

An oral hygiene apparatus for facilitating the accomplishment of an oral hygiene program. The apparatus includes liquid injection ports and a suction opening which are located proximate the bristles provided on the apparatus with the liquid injection ports being coupled to a remote source of liquid under pressure and the suction opening being coupled to a remote source of negative static pressure. The injected liquid in conjunction with a conventional brushing action will dislodge foreign matter in the oral cavity and the injected liquid along with the dislodged matter are evacuated from the oral cavity via the suction port of the apparatus.

10 Claims, 5 Drawing Figures

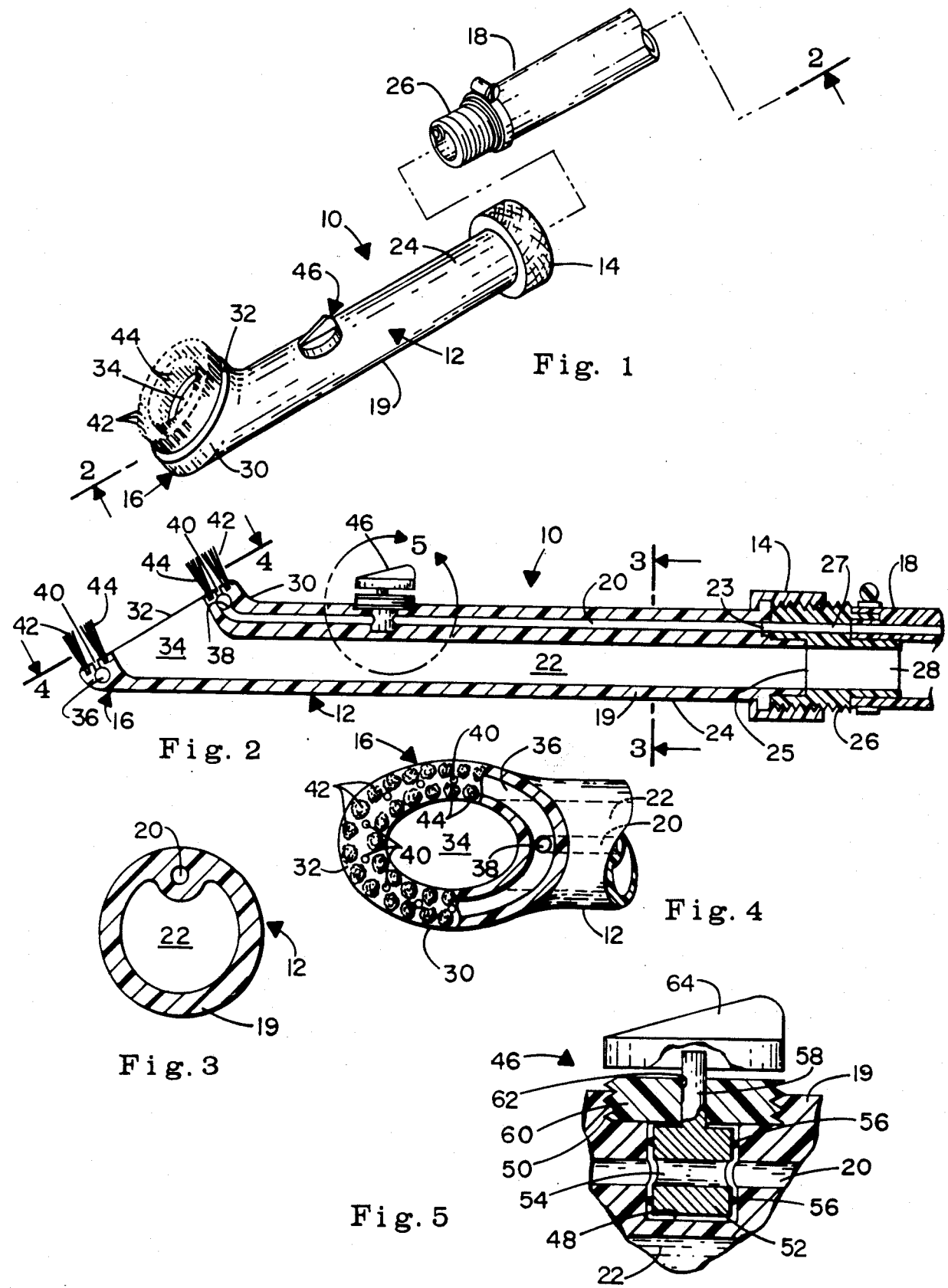

ORAL HYGIENE APPARATUS

BACKGROUND OF THE INVENTION

1. Field of the Invention

This invention relates in general to implements used in the practice of oral hygiene and more particularly to an apparatus which facilitates the practice of oral hygiene by, or in behalf of, medically compromised persons or others who are unable to do a proper job by themselves.

2. Description of the Prior Art

The practice of oral hygiene in hospitals, nursing homes, day care centers and the like, has always been a rather vague and ill defined procedure. Some people in such institutions are, of course, able to care for themselves by using conventional tooth brushes and commercially available oral hygiene products such as toothpaste, mouth washes, and the like. However, others both in and out of such institutions are largely or totally dependent on others. For example, people suffering from arthritis, stroke victims, and other medically compromised people, may find it difficult to hold and manipulate a tooth brush while other more severely ill people such as senile or comatose patients simply cannont maintain their own oral hygiene programs.

Those people who find it difficult to hold and manipulate a conventional tooth brush are very often ineffective when it comes to accomplishing adequate oral hygiene. Similarly, those attempting to help the people who are unable to help themselves, such as the staff personnel of a hospital or nursing home, or the family of such a person, are not trained in the techniques needed for administering proper oral hygiene to others. And, it is very awkward, messy, and otherwise difficult for untrained medical or lay people to help others with the needed oral hygiene. As a result, very often even in medical institutions, the practice of oral hygiene is inadequate and in some cases non-existant.

To the best of my knowledge, no device, apparatus or method has been devised to aid those people who find it difficult to help themselves in accomplishing proper oral hygiene and to faciliate the task of those people who are attempting to help those who are unable to help themselves.

SUMMARY OF THE INVENTION

In accordance with the present invention, a new and improved oral hygiene apparatus is disclosed to facilitate the accomplishment of a proper oral hygiene program by people who find it difficult to use conventional procedures and by people who are trying to help those people who are unable to help themselves.

The apparatus includes a handle having separated first and second passages extending axially therethrough with a coupling means on one end for connecting the first passage to a source of liquid under pressure and for connecting the second passage to a source of negative static pressure. A brush head is integrally formed on the opposite end of the handle and the head is configured to define a substantially planar surface from which an array of bristle means extends normally. The brush head further defines a manifold which is in liquid communication with the first passage of the handle and at least one discharge port which extends from the manifold so as to open up onto the planar surface defined by the head. A relatively large suction opening is also proved in the planar surface of the brush head and extends so as to be in communication with the second passage of the handle. A flow control valve is provided in the handle for controlling and/or regulating the flow of liquid through the first passage provided in the handle.

The above described oral hygiene apparatus can be used much in the same manner as a conventional tooth brush, e.g., with a brushing action. However, the apparatus provides additional benefits of injecting an irrigating liquid and/or lavaging solution into the vicinity of the brushing action and this occurs similtaneously with the brushing action. The simultaneously accomplished brushing and liquid injection results in a more thorough cleaning than can be accomplished if those operations are accomplished separately. Further, the injected liquid and/or lavaging solution along with plaque, tartar, and food debris, which are broken up and otherwise dislodged by the above described actions of the apparatus, are continuously being evacuated from the oral cavity by virtue of the suction provided at the brush head of the apparatus.

In view of the above, it will be appreciated that a person who finds it difficult to hold and manipulate a conventional tooth brush and accomplish an adequate oral hygiene program can accomplish a much improved oral hygiene program with considerably reduced effort by using the apparatus of the present invention. Similarly, a person that is attempting to help someone who is unable to accomplish his or her own oral hygiene program will, by using the apparatus of the present invention, be able to easily accomplish a significantly improved oral hygiene program with a minimum amount of training and without the attending mess that usually accompanies the use of conventional techniques and equipment.

Accordingly, it is an object of the present invention to provide a new and improved oral hygiene apparatus for facile and improved accomplishment of an oral hygiene program.

Another object of the present invention is to provide a new and improved oral hygiene apparatus for facilitating the accomplishment of a satisfactory oral hygiene program by persons who find it difficult to hold and manipulate a conventional tooth brush.

Another object of the present invention is to provide a new and improved oral hygiene apparatus by which a rotatably untrained person can easily accomplish a satisfactory oral hygiene program on others who are unable to accomplish that task for themselves.

Another object of the present invention is to provide a new and improved oral hygiene apparatus which is configured for simultaneous accomplishment of a brushing action and injection under pressure of an irrigating liquid and/or lavage solution into the vicinity of the brushing action.

Another object of the present invention is to provide a new and improved oral hygiene apparatus of the above described character which is further configured to simultaneously evacuate the oral cavity to carry away the injected liquid and/or lavage solution along with plaque, tartar, and for debris which are broken up or otherwise dislodged by the actions of the apparatus.

The foregoing and other objects of the present invention as well as the invention itself, may be more fully understood from the following description when read in conjunction with the accompanying drawings.

BRIEF DESCRIPTION OF THE DRAWINGS

FIG. 1 is a perspective view of the oral hygiene apparatus of the present invention and showing an example of a hose means for supplying liquid under pressure to the oral hygiene apparatus and for connection of a negative static pressure thereto.

FIG. 2 is an enlarged sectional view taken along the line 2—2 of FIG. 1 and showing the hose means connected to the oral hygiene appartus.

FIG. 3 is an enlarged sectional view taken along the line 3—3 of FIG. 2.

FIG. 4 is an enlarged view taken along the line 4—4 of FIG. 2 with portions being broken away to show the various features thereof.

FIG. 5 is an enlarged sectional view better showing the structure encircled at 5 in FIG. 2.

DESCRIPTION OF THE PREFERRED EMBODIMENT

Referring more particularly to the drawings, FIG. 1 shows the oral hygiene apparatus of the present invention which is identified in its entirety by the reference numeral 10. The apparatus 10 includes, as will hereinafter be described in detail, a handle structure 12 having a coupling means 14 on one end thereof and a brush head 16 on the other end. FIG. 1 also shows a hose means 18 for supplying liquid under pressure to the apparatus and for coupling a negative static pressure thereto for reasons which will become apparent as this description progresses.

As shown best in FIGS. 2 and 3, the handle structure 12 is in the form of an elongated tubular body 19 which is especially molded or otherwise formed to provide a first relatively small passage 20 and a second relatively large passage 22 which are separated from each other and both extend axially of the handle. The first relatively small passage 20 opens as at 23 on one end 24 of the handle and the second relatively large passage 22 opens as at 25 on that same end 24 of the handle structure 12.

The coupling means 14, such as the illustrated nut, is suitably mounted on the end 24 of the handle structure 12 and is internally threaded for connection to a special fitting 26 provided on the hose means 18. When the couplng means 14, e.g., nut, is connected to the hose 18, the first passage 20 of the handle 12 is in liquid communication with a similar passage 24 formed in the special fitting 26 and in the hose 18. The second passage 22 of the handle 12 is similarly coupled to a central passage 28 of the hose means 18. The other end (not shown) of the hose means 18 is for connection to a suitable remote source of liquid under pressure and to a mechanism, such as a suction pump. The liquid under pressure, such as from a municipal water supply or a pump (not shown) is directed through the passage 27 of the hose means 18 to the first passage 20 of the handle structure 12. Similarly, the negative static pressure produced, for example, by the above mentioned suction pump (not shown) is coupled to the second passage 22 of the handle structure 12 via the central passage 28 of the hose means 18.

It will be understood that the illustrated hose means 18 is just an example of a means for accomplishing the intended purpose in that various other means could be employed for connecting a liquid under pressure to the apparatus 10 and for coupling a negative static pressure thereto. For example, the end 24 of the handle structure 12 could be divided into two separate boss-like structures (not shown) each having a coupling nut for connection of separate liquid supply and vacuum hoses thereto.

In any case, the handle structure 12 is configured to receive liquid under pressure in the first relatively small passage 20 thereof and to have a negative static pressure in the second relatively large passage 22.

The previously mentioned brush head means 16 is provided on the other end of the handle structure 12 and is preferably formed integrally therewith. The brush head 16 includes an enlarged body 30 of a generally oval configuration and defining a substantially planar surface 32 which slopes angularly and upwardly from the forward most end of the apparatus 10 toward the end 24 of the handle. A relatively large centrally located suction opening 34 of generally oval shape is formed centrally in the planar surface 32 of the enlarged body 30 and that opening 34 is in communication with the second passage 22 formed in the handle structure 12.

An endless manifold 36 is formed in the body 30 so as to surround the central opening 34 and the manifold is provided with an inlet 38 which places the manifold in liquid receiving communication with the first passage 20 provided in the handle structure 12. An oval array of incrementally spaced liquid discharge ports 40 extend from the manifold 36 and open onto the planar structure 32 of the brush head body 30.

Bristle means in the preferred form of an outer oval array formed of a plurality of tufts 42 and an inwardly disposed oval array formed of a plurality of tufts 44, are supportingly carried in a manner well known in the art, on the body 30 so as to extend substantially normally from the planar surface 32. The outer and inner bristle tuft arrays 42 and 44 are concentric with the suction opening 34, and the concentric spacing therebetween in such that the oval array of liquid discharge ports 40 are concentrically located between the bristle tuft arrays.

From the above, it will be seen that when the apparatus 10 is being used, liquid under pressure will be emitted from the plurality of discharge ports 40 into the immediate vicinity of the bristle tuft arrays 42 and 44 and, in addition to wetting the bristles, the liquid will continuously flush the bristles to provide a continuous cleaning thereof. Also, the liquid will be injected into the oral cavity of the person using the apparatus or upon which the apparatus is being used thus providing a cleaning and irrigating action which augments the brushing action provided by manipulation of the apparatus by the user. It will be appreciated that the injected liquid may be water or it may be a lavage solution containing any of several medically improved ingredients.

The injected irrigating liquid, or lavage solution, will be evacuated from the oral cavity along with any broken up or otherwise dislodged plaque, tartar, food particles, and the like, by means of negative static pressure, or suction, presented at the central opening 34 of the brush head body 30.

As best seen in FIG. 5, the apparatus 10 further includes a valve means 46 which is mounted in the handle structure 12. The valve means 46 is manually operable for controlling, e.g. turning off or on and/or regulating, the flow of liquid under pressure which passes through the first passage 20 of the handle 12 on its way to the brush head 16.

A blind bore 48 is molded, drilled, or otherwise formed in the handle 19 so as to transversely intersect the first passage 20 of the handle, and an internally threaded counterbore 50 is formed at the mouth of the blind bore 48. A cylindrical valve body 52 is located within the blind bore 48 for rotational movement therein. The valve body 52 has a transverse passage 54 formed therethrough which is moved into axial alignment with the passage 20 to permit liquid flow in the first passage 20 of the handle and, upon rotation of the valve body 52, will be rotated out of axial alignment for flow regulating and liquid shut off purposes. The valve body 52 is provided with suitable O-ring type seals 56 for leakage prevention.

A reduced diameter stem 58 extends axially from the valve body 52 so as to pass through the counterbore 50 and protrude therefrom. An externally threaded collar 60 is mounted in the counterbore 50 to prevent axial displacement of the valve body 52, and the stem 58 of the valve body extends through a central aperture 62 provided in the collar. A suitable knob 64 is carried on the extending end of the valve stem 58 by which an operator can manually rotate the valve body to the desired positions.

While the principles of the invention have now been made clear in the illustrated embodiment, there will be immediately obvious to those skilled in the art, many modifications of structure, arrangements, proportions, the elements, materials and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claimed is:

1. An oral hygiene apparatus for facilitating the accomplishment of an oral hygiene program, said apparatus being connectable to a hose means for supplying liquid under pressure from a remote source to said apparatus and for coupling a negative static pressure from a remote source thereto, said apparatus comprising:
   (a) a handle defining separated first and second passages which extend axially therethrough;
   (b) coupling means on one end of said handle for connection to the hose means for supplying the liquid under pressure to the first passage of said handle and for coupling the negative static pressure to the second passage thereof; and
   (c) brush head means on the opposite end of said handle and including a body defining a substantially planar surface with a suction opening which opens centrally onto the planar surface and is in communication with the second passage of said handle, said brush head means having bristle means which includes a plurality of bristle tufts which extend from the planar surface of said body and are arranged in a first concentric array about the suction opening of said body and a second outwardly spaced concentric array, said body having at least one liquid discharge port which opens onto the planar surface defined by said body between the first and second concentric arrays of said bristle means and is in liquid receiving communication with the first passage of said handle.

2. An oral hygiene apparatus as claimed in claim 1 and further comprising valve means mounted in said handle and being operable for controlling the flow of liquid through the first passage of said handle.

3. An oral hygiene apparatus as claimed in claim 1 wherein said brush head means is integrally formed on the opposite end of said handle means.

4. An oral hygiene apparatus as claimed in claim 1 wherein said bristle means of said brush head means extends substantially normally from the planar surface defined by said body.

5. An oral hygiene apparatus for facilitating the accomplishment of an oral hygiene program, said apparatus being connectable to a hose means for supplying liquid under pressure from a remote source to said apparatus and for coupling a negative static pressure from a remote source thereto, said apparatus comprising:
   (a) a handle defining separate first and second passages which extend axially therethrough;
   (b) coupling means on one end of said handle for connection to the hose means for supplying the liquid under pressure to the first passage of said handle and for coupling the negative static pressure to the second passage of said handle;
   (c) a brush head body on the opposite end of said handle and configured to define a substantially planar surface, said body having a suction opening formed centrally in the planar surface thereof with the suction opening being in communication with the second passage of said handle;
   (d) bristle means on said brush head body and being in the form of a plurality of bristle tufts arranged in at least one concentric array about the suction opening formed in said body; and
   (e) said brush head body having an endless manifold formed therein which is in liquid receiving communication with the first passage of said handle, said body further defining a plurality of liquid discharge ports which extend in spaced increments from the manifold and open onto the planar surface of said body concentrically with respect to the suction opening formed in said body.

6. An oral hygiene apparatus as claimed in claim 5 wherein said bristle means comprises a first concentric array formed of a plurality of bristle tufts and an outwardly spaced second concentric array formed of another plurality of bristle tufts.

7. An oral hygiene apparatus as claimed in claim 6 wherein the concentrically arranged plurality of liquid discharge ports open onto the planar surface defined by said brush head body between the first and second concentric arrays of bristle tufts of said bristle means.

8. An oral hygiene apparatus as claimed in claim 5 and further comprising a manually operable valve means in said handle for controlling the flow of liquid under pressure through the first passage of said handle.

9. An oral hygiene apparatus for facilitating the accomplishment of an oral hygiene program, said apparatus comprising:
   (a) hose means for connection to a remote source of liquid under pressure and a remote source of negative static pressure;
   (b) a handle defining separated first and second passages which extend axially therethrough, said handle having one end coupled to said hose means for supplying the liquid under pressure to the first passage of said handle and for coupling the negative static pressure to the second passage thereof; and
   (c) brush head means on the opposite end of said handle and including a body defining a substantially planar surface with a suction opening which opens centrally onto the planar surface and is in communication with the second passage of said handle, said brush head means having bristle means which includes a plurality of bristle tufts which extend substantially normally from the planar surface of said body and are arranged in a first array concentrically about the suction opening of said body and an outwardly spaced second array concentrically about the suction opening of said body, said body having at least one liquid discharge port which opens onto the planar surface of said body between the first and second arrays of bristle tufts of said bristle means and is in liquid receiving communication with the first passage of said handle.

10. An oral hygiene apparatus as claimed in claim 9 and further comprising a manually operable valve means in said handle for controlling the flow of liquid under pressure through the first passage of said handle.

* * * * *